United States Patent [19]

Harandi et al.

[11] Patent Number: 4,851,602
[45] Date of Patent: Jul. 25, 1989

[54] ALKANES AND ALKENES CONVERSION TO HIGH OCTANE GASOLINE

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 179,792

[22] Filed: Apr. 11, 1988

[51] Int. Cl.⁴ .................................................. C07C 2/00
[52] U.S. Cl. .................................... 585/322; 585/415; 585/467; 585/533; 585/323
[58] Field of Search ............... 585/322, 415, 467, 533, 585/323

[56] References Cited

U.S. PATENT DOCUMENTS

| | | | |
|---|---|---|---|
| 3,827,968 | 8/1974 | Givens et al. | 208/49 |
| 3,845,150 | 10/1974 | Yan et al. | 260/673.5 |
| 3,960,978 | 6/1976 | Givens et al. | 585/533 |
| 4,016,218 | 4/1977 | Haag et al. | 585/467 |
| 4,021,502 | 5/1977 | Plank et al. | 260/683.15 |
| 4,350,835 | 9/1982 | Chester et al. | 585/415 |
| 4,579,999 | 4/1986 | Gould et al. | 585/312 |

Primary Examiner—Curtis R. Davis
Attorney, Agent, or Firm—Alexander J. McKillop; Charles J. Speciale; L. G. Wise

[57] ABSTRACT

Method and means are described for the conversion of lower molecular weight paraffins and olefins to high octane gasoline rich in alkylated aromatics. In a two stage process catalyzed by metallosilicate, crystalline, shape selective zeolite comprising a high temperature first stage and a lower temperature second stage, the ratio of olefins to paraffins in the second stage is maintained at a level sufficient to maintain essentially isothermal reaction conditions. Novel means for effecting the conversion include transport riser reactor and turbulent bed reactor combination.

32 Claims, 6 Drawing Sheets

ALKANES AND ALKENES CONVERSION TO HIGH OCTANE GASOLINE

This invention relates to method and means for the conversion of light paraffins and olefins to high octane gasoline. More particularly, the invention relates to a process and means for the conversion of hydrocarbon mixtures of light paraffins and olefins to gasoline boiling range products rich in aromatics.

BACKGROUND OF THE INVENTION

Conversion of olefins to gasoline and/or distillate product is disclosed in U.S. Pat. Nos. 3,960,978 and 4,021,502 (Givens, Plank and Rosinski) wherein gaseous olefins in the range of ethylene to pentene, either alone or in admixture with paraffins, are converted into an olefinic gasoline blending stock by contacting the olefins with a catalyst bed made up of ZSM-5 or related zeolite. In U.S. Pat. Nos. 4,150,062 and 4,227,992 Garwood et al discloses the operating conditions for the Mobil Olefin to Gasoline/Distillate (MOGD) process for selective conversion of $C_3+$ olefins. A fluidized bed process for converting ethene-containing light olefinic streams, sometimes referred to as the Mobil Olefin to Gasoline (MOG) process is described by Avidan et al in U.S. Patent Application No. 006,407, filed 23 Jan. 1987 now U.S. Pat. No. 4,746,762. The phenomena of shape-selective polymerization are discussed by Garwood in ACS Symposium Series No. 218, Intrazeolite Chemistry, "Conversion of $C_2-C_{10}$ to Higher Olefins over Synthetic Zeolite ZSM-5", 1983 American Chemical Society. U.S. Pat. No. 3,827,968 (Givens et al) discloses a two stage operation wherein a mixed feed containing paraffins and olefins is upgraded in the absence of added hydrogen to a highly aromatic gasoline product. In a first stage oligomerization reaction, olefins are upgraded to higher molecular weight liquid hydrocarbons under relatively mild conditions with a catalyst having the structure of ZSM-5. In a second stage, said liquid hydrocarbons are converted to an aromatic product. A gas phase highly paraffinic stream is withdrawn as by-product from the first stage.

In the process for catalytic conversion of olefins to heavier hydrocarbons by catalytic oligomerization using an acid crystalline metallosilicate zeolite, such as ZSM-5 or related shape selective catalyst, process conditions can be varied to favor the formation of either gasoline or distillate range products. In the gasoline operating mode, or MOG reactor system, ethylene and the other lower olefins are catalytically oligomerized at elevated temperature and moderate pressure. Under these conditions ethylene conversion rate is greatly increased and lower olefin oligomerization is nearly complete to produce an olefinic gasoline comprising hexene, heptene, octene and other $C_6+$ hydrocarbons in good yield.

The olefins contained in an FCC gas plant are an advantageous feed for MOG. U.S. Pat. No. 4,090,949 discloses upgrading olefinic gasoline by conversion in the presence of carbon hydrogen-contributing fragments including olefins and a zeolite catalyst and where the contributing olefins may be obtained from a gas plant. U.S. Pat. Nos. 4,471,147 and 4,504,691 disclose an MOG/D process using an olefinic feedstock derived from FCC effluent. In these two latter patents the first step involves prefractionating the olefinic feedstock to obtain a gaseous stream rich in ethylene and a liquid stream containing $C_3+$ olefin.

The conventional MOG process design is concerned with converting ethylene in a fuel gas stream, such as an FCC off-gas, to gasoline. Motor octane of the gasoline produced is generally about 85. Typically, paraffins conversion under MOG process conditions is not significant thereby constraining the utilization of potential feedstocks available from FCC operations and requiring substantial recycle of paraffins to the FCC main column.

Accordingly, it is an object of this invention to provide a process for the conversion of mixtures of paraffins and olefins to high octane gasoline incorporating the conversion of paraffins and olefins.

It is another object of the present invention to provide a process for the production of high octane gasoline rich in alkylated aromatics.

Yet another object of the present invention is to provide a process for the production of gasoline with higher olefin conversion.

Another object of the instant invention is to provide a novel reactor system for the conversion of paraffinic and olefinic hydrocarbon mixtures to high octane gasoline rich in aromatics.

SUMMARY OF THE INVENTION

The surprising discovery has been made that mixtures of alkanes and alkenes can be converted to high octane gasoline rich in alkylated aromatics representing high alkene conversion in a process combining an initial high temperature aromatization step followed by a lower temperature oligomerization and alkylation step. The achievement is realized when the alkene content in the initial high temperature step is maintained at a concentration sufficient to provide a heat of reaction large enough to balance the endothermic reaction of the alkanes while maintaining the overall reaction at a high temperature. The reaction in both conversion zones is conducted in contact with acidic, medium pore, crystalline metallosilicate zeolite as catalyst. Uniquely, aromatics formed in the first reaction zone are alkylated and alkenes oligomerized to produce high octane gasoline.

More particularly, the invention comprise an improved process for the conversion of lower alkane and alkene hydrocarbons to high octane gasoline comprising:

(a) contacting a hydrocarbon feedstock comprising lower alkanes and alkenes with a fluidized bed of acidic, shape selective metallosilicate catalyst in a first conversion zone under high temperature alkane conversion conditions wherein said feedstock contains an amount of lower alkene sufficient to provide an exotherm sufficient to maintain near isothermal reaction conditions whereby an effluent stream is produced comprising higher aliphatic hydrocarbons rich in aromatics;

(b) contacting said effluent stream and, optionally, an alkene feedstock with a fluidized bed of acidic, metallosilicate catalyst in a second conversion zone at low temperature under oligomerization and alkylation conditions whereby a $C_5+$ gasoline boiling range product is produced rich in alkylated aromatics.

The present invention is implemented in a novel reactor system for the conversion of alkanes and alkenes to $C_5+$ gasoline boiling range hydrocarbons rich in aromatics, comprising in combination:

first reactor means for containing a fluidized bed of metallosilicate catalyst and hydrocarbon feedstock at high temperature reaction conditions;

heater means operatively connected to said first reactor for receiving and preheating a portion of said hydrocarbon feedstock;

second reactor means for containing a fluidized bed of metallosilicate catalyst at low temperature operatively connected to said first reactor means to receive effluent therefrom;

heat exchange means for cooling first reactor effluent receivably connected to said first reactor and in communication with said second reactor;

catalyst regenerator reactor means operatively connected to said first and second reactor means for regenerating spent catalyst therefrom;

separator means operatively connected to said second reactor to receive effluent therefrom and separate product.

DETAIL DESCRIPTION OF THE INVENTION

In one embobiment of the present invention the MOG process is improved to produce high olefin conversion as part of a unique process for high octane gasoline production. The MOG process is well-known in the petroleum refining arts and provides a system for upgrading light olefins, such as FCC product components, to liquid hydrocarbons, utilizing a continuous process for producing fuel products by oligomerizing olefinic components to produce higher hydrocarbon products for use as fuel or the like. The preferred MOG feedstock contains $C_2$-$C_4$ alkenes (mono-olefin) in the range of about 10 to 90 wt %. Nondeleterious components, such as methane and other paraffins and inert gases, may be present. A particularly useful feedstock is a light gas by-product of FCC gas oil cracking units containing typically 10-40 mol % $C_2$-$C_4$ olefins and 5-35 mol % $H_2$ with varying amounts of $C_1$-$C_3$ paraffins and inert gas, such as $N_2$. The process may be tolerant of a wide range of lower alkanes, from 0 to 90%. Preferred feedstocks contain more than 50 wt % $C_1$-$C_4$ lower aliphatic hydrocarbons, and contain sufficient olefins to provide total olefinic partial pressure of at least 50 kPa.

Conversion of lower olefins, especially ethene, propene and butenes, over HZSM-5 is effective at moderately elevated temperatures and pressures. Operating details for typical olefin oligomerization units are disclosed in U.S. Pat. Nos. 4,456,779; 4,497,968 (Owen et al.) and 4,433,185 (Tabak), incorporated herein by reference.

Catalysts useful in the MOG process and the process of the instant invention include a unique group of metallosilicate zeolites. Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalyst preferred for use in olefins conversion and the process of the present invention includes the medium pore (i.e., about 5-7 angstroms) shape selective crystalline aluminosilicate zeolites having a silica to alumina ratio of about 20:1 or greater, a constraint index of about 1-12, and acid cracking activity (alpha value) of about 2-200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. No. Reissue 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); and 4,375,573 (ZSM-48). The disclosures of these patents are incorporated herein by reference.

While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt % silica, clay and/or alumina binder.

These siliceous zeolites may be employed in their acid forms, ion exchanged or impregnated with one or more suitable metals, such as Ga, Pd, Zn, Ni, Co and/or other metals of Periodic Groups III to VIII. Ni-exchanged or impregnated catalyst is particularly useful in converting ethene under low severity conditions. The zeolite may include other components, generally one or more metals of group IV, IIB, IIIB, VA VIA or VIIIA of the Periodic Table (IUPAC). Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent application Ser. No. 893,522, filed Aug. 4, 1986 by Garwood et al now U.S. Pat. No. 4,717,782, incorporated herein be reference.

Figure 1:
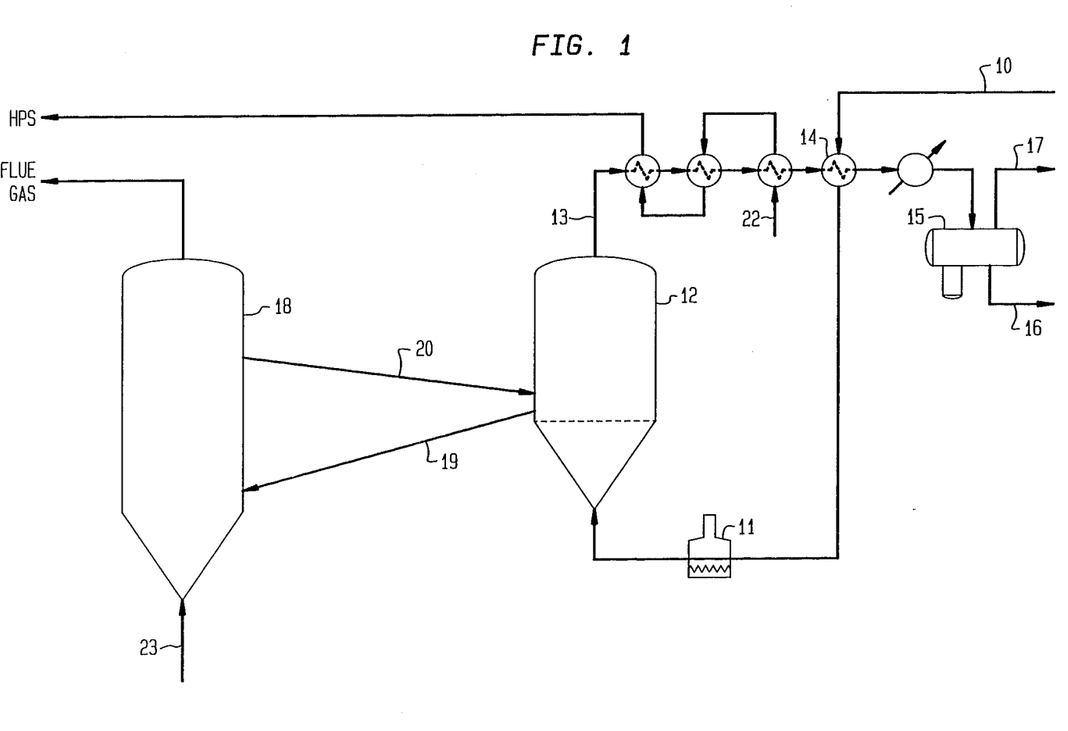
FIG. 1 is a schematic drawing of prior art MOG process design for the conversion of olefins to gasoline.

In FIG. 1, a schematic process flow diagram of prior art Mobil Olefins to Gasoline (MOG) process is presented. An olefins rich feedstock 10 is preheated in heater 11 and passed to MOG reactor 12 containing a fluidized bed of acidic, shape selective metallosilicate catalyst, preferably ZSM-5. The catalyst may have an acid cracking value of about 2 to 35, preferably about 2-5. The feedstock is preheated to a temperature of 65°–175° C. and the reactor operating conditions comprise temperatures of about 215°–535° C. and pressures of about 50–2000kPa and a weight hourly space velocity (WHSV) based on active catalyst of about 0.5-10. The reactor effluent 13 is cooled, optionally in indirect heat exchange with feedstock 14 and cooling water 22 and separated in separator 15 to produce liquid $C_5+$ gasoline 16 and vapor product 17. Spent catalyst is passed to regenerator vessel 18 via line 19 for oxidative regeneration with air 23 and regenerated catalyst is recycled to reactor 12 through line 20. Under these conditions greater than 80% of the lower olefins in the feedstock are converted to higher hydrocarbons.

The conversion of paraffins to aromatics is a highly endothermic reaction which occurs at high temperature. In the MOG process conversion of paraffins is negligible. Olefins conversion in the M-2 Forming process in contact with ZSM-5 catalyst produces aromatics which results in low volumetric gasoline yield. M-2 Forming also produces about 23 weight percent benzene. Considering the above facts it is preferred to convert olefins in the MOG process. However, to convert paraffins part of the olefins are converted to aromatics in order to minimize paraffins conversion reaction section cost. The rest of the olefins are converted in MOG where benzene produced via M-2 Forming is also alkylated. The overall reaction section is integrated into the FCC gas plant to minimize recovery section cost. The result in the present invention is achieved in a dual reactor zone configuration embodying a first high temperature reactor containing paraffins and olefins in a ratio sufficient to provide enough heat of reaction from olefin conversion to balance the paraffins endothermic conversion reaction and maintain the overall reaction at near isothermal conditions. Reactions occurring in the first reactor are primarily dehydrocyclization reactions to produce aromatics. The effluent is passed to a second reaction zone optionally in conjunction with additional olefin feed. The second zone is operated at lower temperature, typically MOG conversion conditions. Second zone conditions favor olefins oligomerization and alkylation of aromatics produced in the first conversion zone. Accordingly, product separated from the second reaction zone includes $C_5+$ gasoline having a motor octane of about 90+, compared to 85 for prior art MOG product. Catalyst employed in the first and second fluidized bed reaction zones is preferably a Gallium-containing ZSM-5.

The feed to the first reactor zone is preheated to a temperature of about 510° C. or greater. Operating conditions for the first zone comprise a ratio of paraffins to olefins in the feedstock of between 0.1 and 5, preferably 0.3 to 2; temperature between 510° and 800° C., preferably 600° C.; pressure between 100 and 2000 kPa, preferably 1300 kPa; WHSV between 0.4 and 400, preferably 1.0. In the second reaction zone, operating conditions follow customary MOG operations, but an operating temperature of about 400° C. is preferred to enhance alkylation of benzene in the effluent from the first reaction zone.

Figure 2:
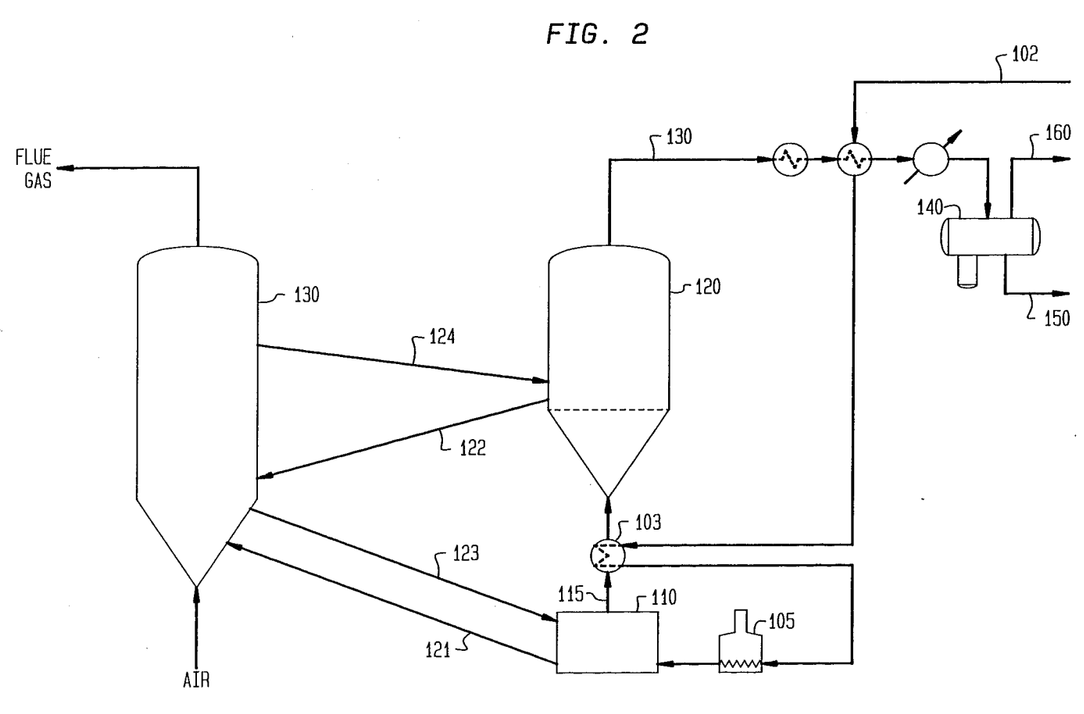
FIG. 2 is a schematic drawing of the basic process design of the instant invention.

Referring to FIG. 2, a schematic of the basic process of the instant invention is presented. Major components comprise feedstock preheater 105, high temperature first fluidized bed reactor vessel 110, second lower temperature fluidized bed reactor vessel 120, catalyst regenerator vessel 130 and product separator 140. Feedstock 102 is passed to preheater 105, preferably through indirect heat exchanger 103. Preheated feedstock is then passed to reactor 110 where under high temperature conditions in contact with zeolite catalyst paraffins and olefins are converted to aromatics and higher hydrocarbons. The effluent is passed via line 115 to fluidized bed reactor 120, preferably following indirect heat exchange with feedstock through heat exchanger 103. In reactor 120 the effluent is converted to $C_5+$ gasoline boiling range hydrocarbons and alkylated aromatics plus ligher hydrocarbons and inerts in contact with zeolite catalyst at relatively lower temperature. Spent catalyst from reactors 110 and 120 is passed to oxidative regenerator vessel 130 via lines 121 and 122 and regenerated catalyst is recycled to the reactors via lines 123 and 124. Effluent from reactor 120 after cooling is passed via line 130 to separator 140. In separator 140, liquid product 150 comprising $C_5+$ high octane gasoline is separated as well as gaseous products comprising $C_4-$ hydrocarbons and inerts 160.

Figure 3:
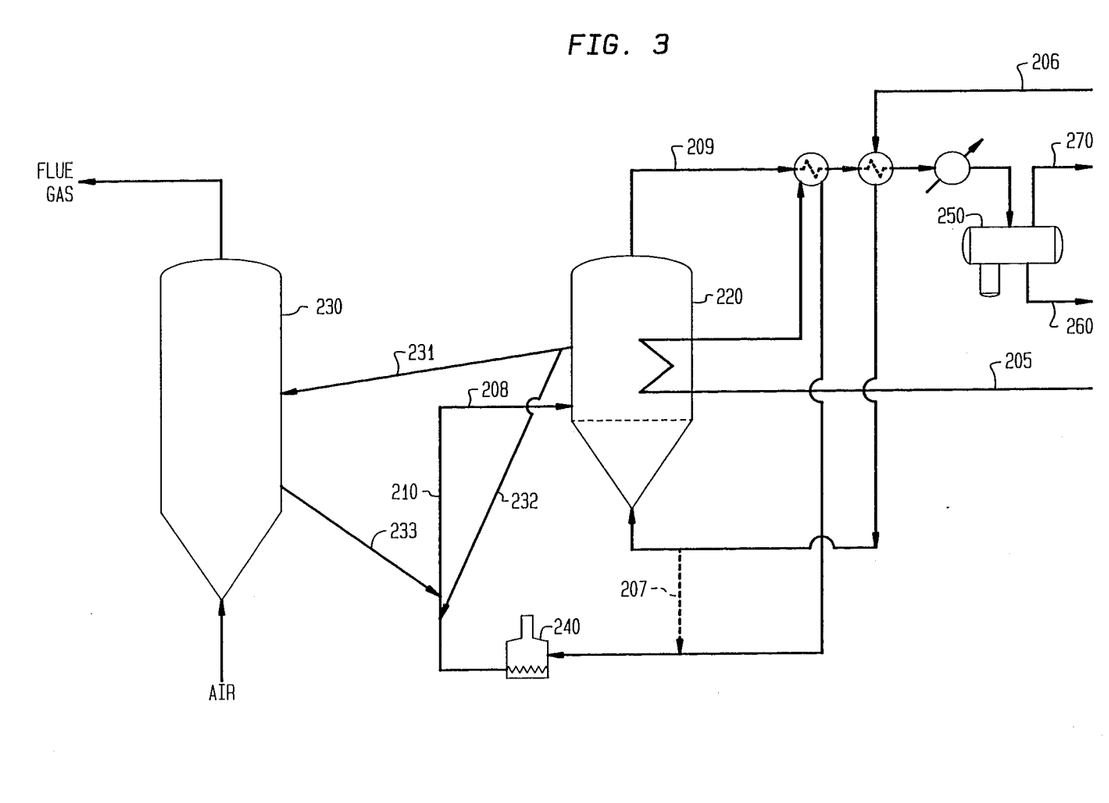
FIG. 3 is a schematic drawing of the instant invention illustrating novel catalyst regeneration and configuration for fuel gas conversion with $C_3$ hydrocarbons.

Referring to FIG. 3, a novel reactor system of the present invention is schematically presented depicting a design for fuel gas and $C_3$ hydrocarbons conversion. Major system components include transport riser reactor 210, turbulent fluidized bed MOG reactor 220, catalyst regenerator vessel 230, preheater 240 and separator 250. $C_3$ hydrocarbon feedstock is pass 205 to riser reactor 210 through preheater 240 for paraffins and olefins conversion, preferably following indirect heat exchange in reactor 220. Fuel gas as feedstock is passed 206 to reactor 220 and, optionally, passed 207 to reactor 210. Effluent from reactor 210 is passed 208 for conversion in reactor 220, the product of which is passed 209 to product separator 250 for product recovery as described to MOG gasoline 260 and vapor product 270. Catalyst regeneration is accomplished by passing 231 a portion of spent catalyst from reactor 220 to oxidative regenerator 230 while another portion is recycled 232 to reactor 210 in conjunction with regenerated catalyst recycled via line 233.

Figure 4:
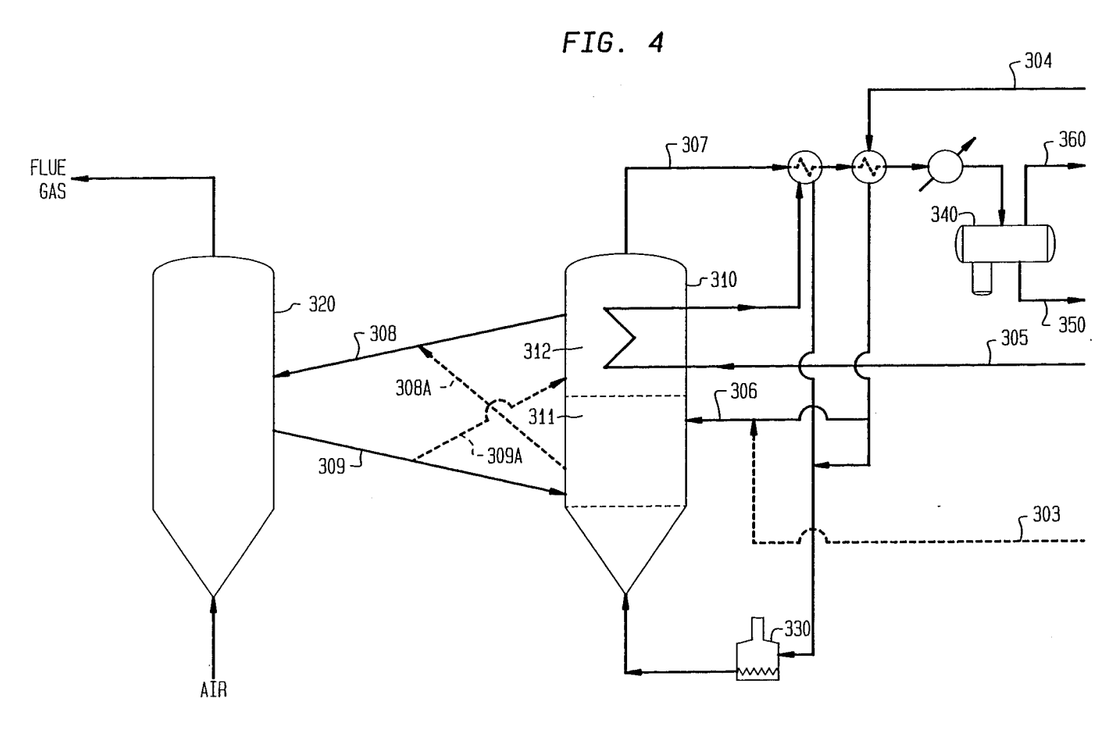
FIG. 4 is a schematic drawing of the instant invention illustrating novel reactor configuration for $C_4$-conversion.

Referring to FIG. 4, a novel reactor system of the present invention is depicted schematically for the conversion of $C_4-$ hydrocarbons. Major components include a single reactor vessel 310 containing separate fluidized bed reactor zones 311 and 312, catalyst regenerator 320, preheater 330 and separator 340. $C_3-C_4$ hydrocarbons are passed 305 to high temperature reactor zone 311 through heater 330 optionally in conjunction with a portion of fuel gas feedstock 304, preferably after indirect heat exchange in reactor zone 312. At least a major portion of fuel gas feedstock is passed to reactor 311 directly via line 306, optionally in conjunction with reformate or crackate feed 303. Following conversion of the feedstock in zones 311 and 312, vessel effluent 307 is cooled and separated in separator 340 to produce $C_{5}+$ high octane gasoline 350 as previously described and vapor product. Catalyst regeneration is accomplished by passing 308 and 308A spent catalyst from zones 312 and 311 to regenerator 320 and recycling 309 and 309A regenerated catalyst to zones 311 and 312.

Figure 5:
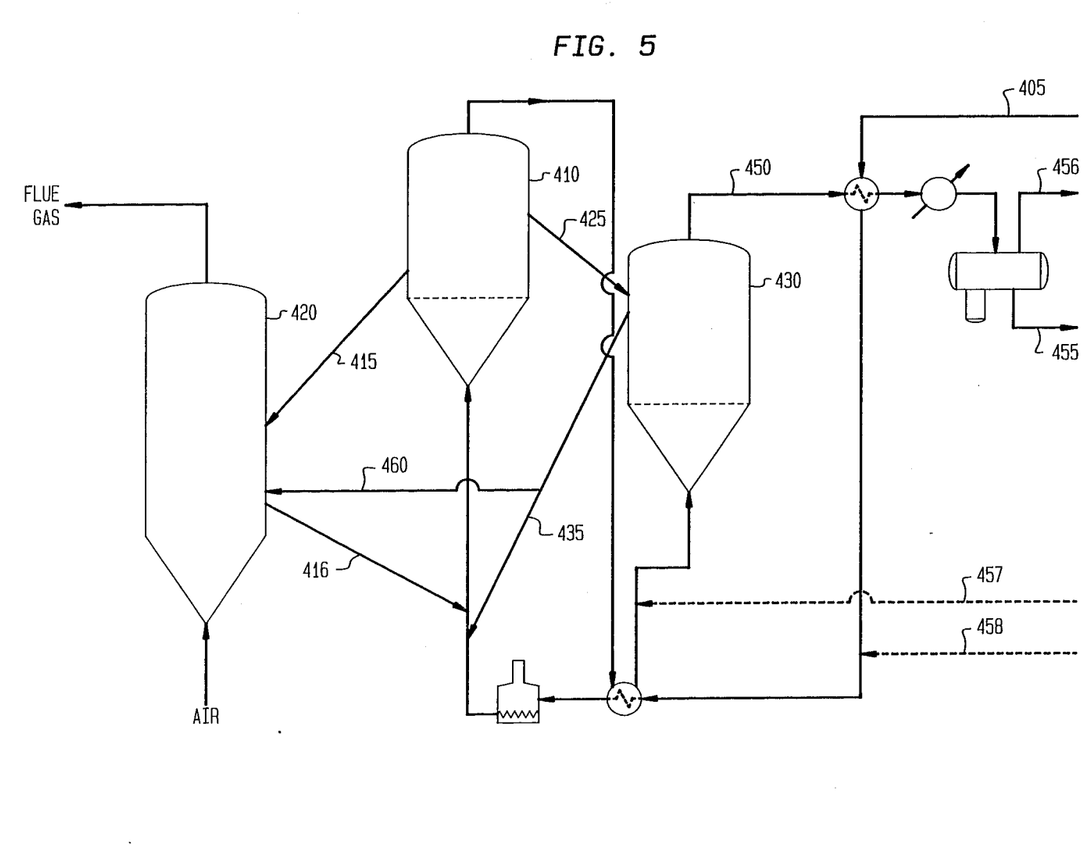
FIG. 5 is a schematic drawing of the instant invention illustrating novel reactor configuration for fuel gas conversion.

FIG. 5 presents an alternative novel process configuration of the present invention particularly applicable to fuel gas conversion as provided to the process via line 405. In this configuration spent catalyst from high temperature fluidized bed reactor 410 is passed 415 to catalyst regenerator 420 and regenerated catalyst therefrom is recycled 416 to reactor 410. A portion of spent catalyst from reactor 410 is also passed 425 to fluidized bed reactor 430 and spent catalyst therefrom is recycled 435 to reactor 410 or optionally passed 460 to regenerator 420. Product effluent 450 is recovered as previously describedas MOG gasoline 455 and vapor product 458. Optional feeds to reactor 430 include benzene/methanol 457 and LSR or other paraffins 458.

Figure 6:
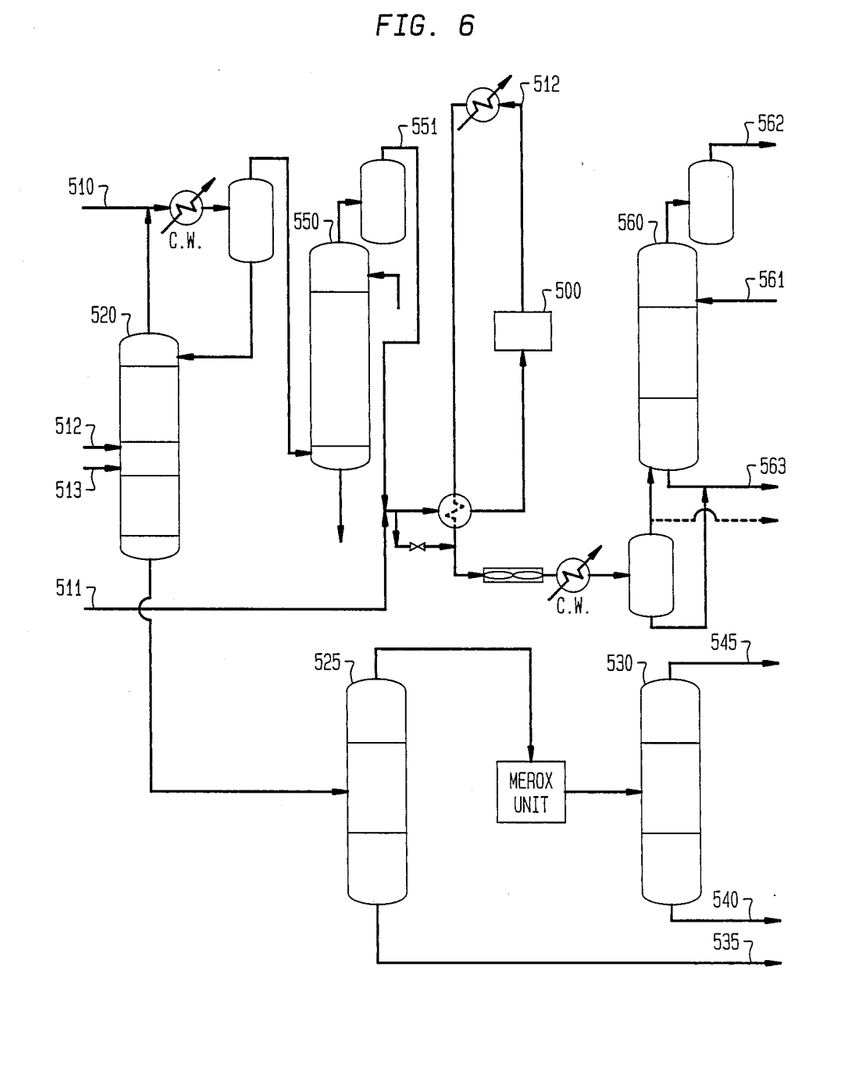
FIG. 6 is a schematic drawing showing the integration of the MOG process into an unsaturated gas plant as in the present invention.

The process of the present invention is readily integrated as an MOG reaction section 500 with unsaturated gas plant to realize significant cost savings as depicted in FIG. 6. Feeds to the plant comprise FCC wild gasoline 510, FCC $C_3$ hydrocarbons 511, gas and liquid feeds 512 and 513 processed in deethanizer, debutanizer and depropanizer 520,525 and 530 to provide FCC and MOG gasoline 535, FCC and MOG $C_4$'s 540 and $C_3$'s 545. The FCC $C_3$ feedstream 511 is combined with effluent 551 from amine absorber 550 as feedstream to the MOG reaction section 500. The MOG effluent is cooled and treated in sponge absorber 560 with lean oil 561 to provide off gas 562, MOG product and rich oil recycle 563 to FCC main column.

While the invention has been described by reference to specific embodiments, there is no intent to limit the scope of the invention except as described in the following claims.

What is claimed is:

1. A process for the conversion of lower alkane and alkene hydrocarbons to high octane gasoline comprising:
    (a) contacting a hydrocarbon feedstock comprising lower alkanes and alkenes with a fluidized bed of acidic, shape selective metallosilicate catalyst in a first conversion zone under high temperature alkane conversion conditions wherein said feedstock contains an amount of lower alkene sufficient to provide an exotherm sufficient to maintain near isothermal reaction conditions whereby an effluent stream is produced comprising higher aliphatic hydrocarbons rich in aromatics;
    (b) contacting said effluent stream with a fluidized bed of acidic, medium pore metallosilicate catalyst in a second conversion zone at moderate temperature under oligomerization and alkylation conditions whereby a $C_5+$ gasoline boiling range product is produced rich in alkylated aromatics.

2. The process of claim 1 wherein said hydrocarbon feedstock is preheated to a high temperature before passing to said first conversion zone.

3. The process of claim 2 wherein said hydrocarbon feedstock is preheated to a temperature between about 480° and 800° C.

4. The process of claim 1 wherein said second conversion zone moderate temperature oligomerization and alkylation conditions comprise temperature between about 315° and 480° C.

5. The process of claim 4 wherein said temperature is preferably about 400° C.

6. The process of claim 1 wherein said first conversion zone comprises a transport riser fluidized bed conversion zone and said second conversion zone comprises a turbulent fluidized bed conversion zone.

7. The process of claim 1 wherein said alkane and/or alkene hydrocarbon feedstock components comprises $C_2$-$C_4$ hydrocarbons.

8. The process of claim 1 wherein said alkane component of said hydrocarbon feedstock comprises fuel gas.

9. The process of claim 1 further comprising passing spent catalyst from said first and/or second conversion zones to a catalyst regeneration zone under regeneration conditions and recycling regenerated catalyst to said first and/or second conversion zones.

10. The process of claim 9 wherein said regeneration conditions comprise oxydative catalyst regeneration in a common regeneration zone.

11. The process of claim 9 wherein a first portion of said second conversion zone spent catalyst is passed to said regeneration zone, a second portion is passed to transport riser first conversion zone in conjunction with regenerated catalyst from said regeneration zone.

12. The process of claim 9 wherein a first portion of said first conversion zone spent catalyst is passed to said regeneration zone, a second portion is passed to said second conversion zone and regenerated catalyst is recycled to said first conversion zone in conjunction with spent catalyst from said second conversion zone.

13. The process of claim 1 wherein said metallosilicate catalyst comprises aluminosilicate zeolite having the structure of ZSM-5.

14. The process of claim 13 wherein said aluminosilicate contains gallium.

15. The process of claim 1 wherein the ratio of alkane to alkene in said feedstock is between about 0.2 and 5 at a weight hourly space velocity based on active catalyst between 0.4 and 400.

16. The process of claim 15 wherein the ratio of alkane to alkene is preferably about 1.5 at a WHSV of about 1.0.

17. In the process for the conversion of alkenes to gasoline boiling range hydrocarbons comprising contacting a hydrocarbon feedstock rich in lower olefins with an acidic shape selective metallosilicate catalyst under oligomerizing conditions in a conversion zone at a temperature between 215° C. and 535° C. and pressures of about 50 to 2000 kPa and a WHSV of about 0.1–10 whereby $C_5+$ hydrocarbons are produced, the improvement comprising:
    (a) contacting a hydrocarbon feedstock comprising lower alkanes and alkenes with a fluidized bed of acidic, shape selective metallosilicate catalyst in a first conversion zone under high temperature alkane conversion conditions wherein said feedstock contains an amount of lower alkene sufficient to provide an exotherm sufficient to maintain near isothermal reaction conditions whereby an effluent stream is produced comprising higher aliphatic hydrocarbons rich in aromatics;

(b) contacting said effluent stream with a fluidized bed of acidic, metallosilicate catalyst in a second conversion zone at low temperature under oligomerization and alkylation conditions whereby a $C_5+$ gasoline boiling range product is produced rich in alkylated aromatics.

18. The process of claim 17 wherein said hydrocarbon feedstock is preheated to a temperature between about 480° and 800° C.

19. The process of claim 17 wherein said second conversion zone low temperature oligomerization and alkylation conditions comprise temperature between about 315° and 480° C.

20. The process of claim 17 wherein said first conversion zone comprises a transport riser fluidized bed conversion zone and said second conversion zone comprises a turbulent fluidized bed conversion zone.

21. The process of claim 17 wherein said alkane and/or alkene hydrocarbon feedstock components comprises $C_2$-$C_4$ hydrocarbons.

22. The process of claim 17 wherein said alkene component of said hydrocarbon feedstock comprises fuel gas.

23. The process of claim 17 further comprising passing spent catalyst from said first and/or second conversion zones to a catalyst regeneration zone under regeneration conditions and recycling regenerated catalyst to said first and/or second conversion zones.

24. The process of claim 23 wherein said regeneration conditions comprise oxydative catalyst regeneration in a common regeneration zone.

25. The process of claim 23 wherein a first portion of said second conversion zone spent catalyst is passed to said regeneration zone, a second portion is passed to transport riser first conversion zone in conjunction with regenerated catalyst from said regeneration zone.

26. The process of claim 23 wherein a first portion of said first conversion zone spent catalyst is passed to said regeneration zone, a second portion is passed to said second conversion zone and regenerated catalyst is recycled to said first conversion zone in conjunction with spent catalyst from said second conversion zone.

27. The process of claim 17 wherein said metallosilicate catalyst comprises aluminosilicate zeolite having the structure of ZSM-5.

28. The process of claim 27 wherein said aluminosilicate contains gallium.

29. The process of claim 17 wherein the ratio of alkane to alkene in said feedstock is between about 0.2 and 5 at a weight hourly space velocity based on active catalyst between 0.4 and 400.

30. The process of claim 29 wherein the ratio of alkane to alkene is preferably about 1.5 at a WHSV of about 1.0.

31. The process according to claim 1 further comprising combining step (b) effluent stream and alkene feedstock in contact with said fluidized bed of catalyst.

32. The process of claim 17 further comprising, introducing an alkene feedstock into step (b) conversion zone in addition to step (a) effluent stream.

* * * * *